United States Patent [19]

Pfister et al.

[11] Patent Number: 4,541,858
[45] Date of Patent: Sep. 17, 1985

[54] CHLORINATED PHOSPHORYLMETHYLCARBONYL DERIVATIVE PLANT PROTECTION AGENTS

[75] Inventors: Theodor Pfister, Monheim; Ludwig Eue, Leverkusen; Robert R. Schmidt, Bergisch-Gladbach; Gerd Hänssler, Leverkusen, all of Fed. Rep. of Germany

[73] Assignee: Bayer Aktiengesellschaft, Leverkusen, Fed. Rep. of Germany

[21] Appl. No.: 591,615

[22] Filed: Mar. 20, 1984

[30] Foreign Application Priority Data

Apr. 12, 1983 [DE] Fed. Rep. of Germany ....... 3313070

[51] Int. Cl.$^4$ ..................... A01N 57/18; A01N 57/22; A01N 57/24; C07F 9/65
[52] U.S. Cl. ......................................... 71/86; 260/937; 260/942; 260/943; 260/944; 260/946; 514/94; 514/110; 514/119; 514/121; 514/125; 548/112; 548/378; 560/226
[58] Field of Search ............... 260/937, 942, 943, 944, 260/946; 548/112; 71/86; 424/200, 209, 211, 212, 214

[56] References Cited

FOREIGN PATENT DOCUMENTS

| 0001018 | 3/1979 | European Pat. Off. . |
| 0001331 | 4/1979 | European Pat. Off. . |
| 1197883 | 5/1965 | Fed. Rep. of Germany . |
| 310406 | 12/1955 | Switzerland . |
| 310397 | 12/1955 | Switzerland . |
| 310398 | 12/1955 | Switzerland . |
| 744360 | 2/1956 | United Kingdom . |

OTHER PUBLICATIONS

Burton et al, Chemical Abstracts, vol. 97 (1982) 216312d.

Primary Examiner—Richard L. Raymond
Attorney, Agent, or Firm—Sprung Horn Kramer & Woods

[57] ABSTRACT

Novel chlorinated phosphorylmethylcarbonyl derivatives of the formula

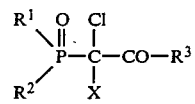

in which
$R^1$ represents an optionally substituted radical from the series comprising alkyl, aryl, aralkyl, alkoxy and aralkoxy and
$R^2$ represents an optionally substituted radical from the series comprising alkoxy and aralkoxy, or
$R^1$ and $R^2$ together represent an alkanedioxy radical,
X represents hydrogen or chlorine and
$R^3$ represents the grouping

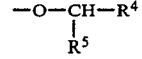

in which
$R^4$ represents hydrogen or optionally substituted alkyl and
$R^5$ represents optionally substituted alkoxycarbonyl radical or an optionally substituted pyrazolyl radical; or
if X represents chlorine, $R^3$ also may represent optionally substituted radical from the series comprising alkyl, cycloalkyl, alkylamino and cycloalkylamino, which possesses fungicidal activity as well as herbicidal activity, but not against rice. Some intermediates are also new.

11 Claims, No Drawings

CHLORINATED PHOSPHORYLMETHYLCARBONYL DERIVATIVE PLANT PROTECTION AGENTS

The invention relates to new phosphorylmethylcarbonyl derivatives, several processes for their preparation and their use as plant protection agents, in particular as herbicides and fungicides.

It is known that certain chlorinated phosphorylacetic acid esters can be used as herbicides (compare, for example, European Pat. No. 1,018). Thus, for example, (1-methyl)-ethyl 2,2-dichloro-2-(diethoxyphosphoryl)acetate can be used for combating weeds. It is also known that certain bis-dithiocarbamates, such as, for example, zinc ethylene-bis-dithiocarbamate, have a fungicidal action (compare U.S. Pat. Nos. 2,457,674 and 3,050,439). However, the action of these compounds is not always adequate, especially when low amounts are employed and in the case of low concentrations.

New chlorinated phosphorylmethylcarbonyl derivatives of the formula (I)

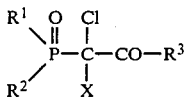  (I)

in which
R¹ represents an optionally substituted radical from the series comprising alkyl, aryl, aralkyl, alkoxy and aralkoxy and
R² represents an optionally substituted radical from the series comprising alkoxy and aralkoxy, or
R¹ and R² together represent an alkanedioxy radical,
X represents hydrogen or chlorine and
R³ represents the grouping $$-O-CH-R^4$$
$$\phantom{-O-C}|$$
$$\phantom{-O-CH-}R^5$$

in which
R⁴ represents hydrogen or optionally substituted alkyl and
R⁵ represents an optionally substituted alkoxycarbonyl radical or an optionally substituted pyrazolyl radical; or
if X represents chlorine, R³ also may represent an optionally substituted radical from the series comprising alkyl, cycloalkyl, alkylamino and cycloalkylamino,
have now been found.

The new compounds of the formula (I) are obtained by a process in which
(a) dichloromethanephosphonic acid derivatives of the formula (II)

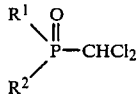  (II)

in which
R¹ and R² represent optionally substituted radicals from the series comprising alkoxy and aralkoxy, or
R¹ and R² together represent an alkanedioxy radical, are reacted with acid halides of the formula (III)

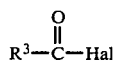  (III)

in which
R³ has the abovementioned meaning and
Hal represents chlorine or bromine, or with isocyanates of the formula (IV)

R⁶—NCO    (IV)

in which
R⁶ represents an optionally substituted radical from the series comprising alkyl and cycloalkyl,
if appropriate in the presence of an acid acceptor and if appropriate in the presence of diluents, or (b) phosphorylmethylcarbonyl compounds of the formula (V)

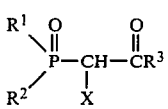  (V)

in which
R¹, R², R³ and X have the abovementioned meanings, are reacted with chlorinating agents, if appropriate in the presence of acid acceptors and if appropriate in the presence of diluents.

The new chlorinated phosphorylmethylcarbonyl derivatives of the formula (I) are distinguished by a high herbicidal and fungicidal activity.

Surprisingly, the active compounds of the formula (I) according to the invention are superior to the chlorinated phosphorylacetic acid esters already known (according to European Pat. No. 1,018) against economically important graminaceous weeds in dicotyledonous crops, such as cotton, soy bean, sugarbeet and groundnut. They also have a better systemic action against plant diseases than the bis-thiocarbamates already mentioned (according to U.S. Pat. Nos. 2,457,674 and 3,050,439).

The invention preferably relates to the new chlorinated phosphorylmethylcarbonyl derivatives of the formula (I),
in which
R¹ represents radicals from the series comprising alkyl with up to 6 carbon atoms, alkoxy with up to 6 carbon atoms and aralkyl and aralkoxy with 6 to 10 carbon atoms in the aryl part and up to 2 carbon atoms in the alkyl part [such as, in particular, benzyl, phenylethyl, benzyloxy and phenylethoxy], in each case optionally monosubstituted or polysubstituted by halogen [such as, in particular, fluorine, chlorine and/or bromine] or C₁-C₄-alkoxy, or represents phenyl which is optionally monosubstituted or polysubstituted by halogen [such as, in particular, fluorine, chlorine and/or bromine], nitro, C₁-C₄-alkyl, C₁-C₄-alkoxy and/or C₁-C₄-alkoxycarbonyl, and
R² represents alkoxy with up to 6 carbon atoms and aralkoxy with 6 to 10 carbon atoms in the aryl part and up to 2 carbon atoms in the alkyl part [such as, in particular, benzyloxy or phenylethoxy], in each case optionally monosubstituted or polysubstituted by halogen [such as, in particular, fluorine, chlorine and/or bromine] or C₁-C₄-alkoxy, or R[1] and R[2] together represent a branched or straight-chain alkanedioxy radical with 2 to 5 carbon atoms in the alkyl part, X represents hydrogen or chlorine and R[3] represents the grouping

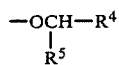

in which

R[4] represents hydrogen or alkyl with up to 4 carbon atoms and

R[5] represents an alkoxycarbonyl radical with up to 4 carbon atoms in the alkyl part, or represents an optionally substituted pyrazolyl radical

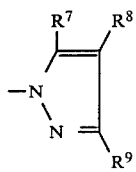

wherein

R[7] and R[9] are identical or different and represent hydrogen or $C_1-C_4$-alkyl and R[8] represents hydrogen, halogen [such as, in particular, chlorine] or $C_1-C_4$-alkyl; or if X represents chlorine, R[3] also may represent alkyl with up to 8 carbon atoms, which is optionally monosubstituted or polysubstituted by halogen, [such as, in particular, fluorine, chlorine and/or bromine], $C_1-C_4$-alkoxy and/or $C_3-C_6$-cycloalkyl, or represents cycloalkyl with 3 to 6 carbon atoms, which is optionally monosubstituted or polysubstituted by $C_1-C_3$-alkyl, or alkylamino with up to 6 carbon atoms in the alkyl part or cycloalkylamino with 3 to 6 carbon atoms.

The invention particularly relates to compounds of the formula (I)

in which (A)

R[1] represents n-propoxy, i-propoxy, n-butoxy, i-butoxy, sec.-butoxy or tert.-butoxy, R[2] represents n-propoxy, i-propoxy, n-butoxy, i-butoxy, sec.-butoxy or tert.-butoxy, X represents chlorine and R[3] represents n-propyl, i-propyl, n-butyl, i-butyl, sec.-butyl, tert.-butyl, cyclopropyl, n-propylamino, i-propylamino, n-butylamino, i-butylamino, sec.-butylamino or tert.-butylamino, or (B)

R[1] represents n-propoxy, i-propoxy, n-butoxy, i-butoxy, sec.-butoxy, tert.-butoxy or phenyl, R[2] represents n-propoxy, i-propoxy, n-butoxy, i-butoxy, sec.-butoxy or tert.-butoxy, X represents chlorine and R[3] represents the grouping

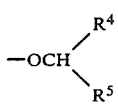

in which

R[4] represents methyl or ethyl and

R[5] represents methoxycarbonyl, ethoxycarbonyl, n-propoxycarbonyl, i-propoxycarbonyl, n-butoxycarbonyl, i-butoxycarbonyl, sec.-butoxycarbonyl or tert.-butoxycarbonyl, or (C)

R[1] represents n-propoxy, i-propoxy, n-butoxy, i-butoxy, sec.-butoxy, tert.-butoxy or phenyl, R[2] represents n-propoxy, i-propoxy, n-butoxy, i-butoxy, sec.-butoxy or tert.-butoxy, X represents hydrogen or chlorine and R[3] represents the grouping

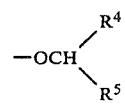

in which

R[4] represents hydrogen, methyl, ethyl, n-propyl or i-propyl and

R[5] represents an optionally substituted pyrazolyl radical

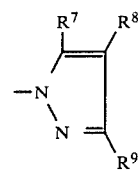

wherein

R[7] and R[9] are identical or different and represent hydrogen or methyl and

R[8] represents hydrogen or chlorine.

If, for example, O,O-di-n-propyl dichloromethanephosphonate and cyclohexylcarboxylic acid chloride or cyclohexyl isocyanate are used as starting substances, the course of the reaction in process variant (a) according to the invention can be represented by the following equation:

(a) 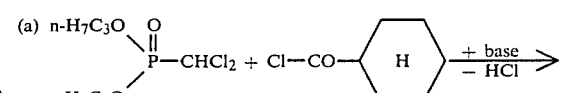

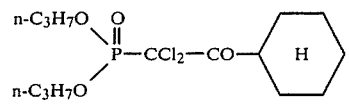

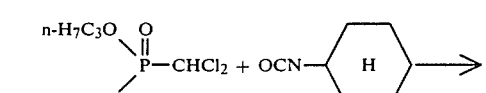

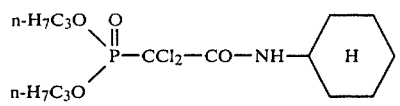

If, for example, sodium hypochlorite is used as the chlorinating agent and 1-(1-pyrazol-1-yl)-ethyl O,O-din-propoxy-phosphoryl-acetate is used as the starting substance, the course of the reaction in process variant (b) according to the invention can be represented by the following equation:

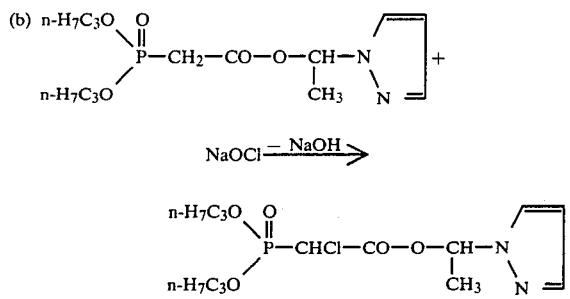

Formula (II) provides a definition of the dichloromethanephosphonic acid derivatives to be used as starting substances. In this formula, $R^1$ and $R^2$ represent optionally substituted radicals from the series comprising alkoxy and aralkoxy, or together represent an alkanedioxy radical. The preferred and particularly preferred definition of these radicals have already been mentioned in the context of the definition of the substituents for formula (I).

Examples which may be mentioned of the compounds of the formula (II) are:

TABLE 1

$$\begin{array}{c} R^1 \\ \phantom{R^1}\diagdown\!\!\!\!\parallel\!\!O \\ \phantom{R^1}\phantom{\diagdown}P\!\!-\!\!CHCl_2 \\ \phantom{R^1}\diagup \\ R^2 \end{array} \qquad (II)$$

| $R^1$ | $R^2$ |
|---|---|
| —OC$_3$H$_7$—n | —OC$_3$H$_7$—n |
| —OC$_3$H$_7$—iso | —OC$_3$H$_7$—iso |
| —OC$_4$H$_9$—n | —OC$_4$H$_9$—n |
| —OC$_4$H$_9$—iso | —OC$_4$H$_9$—iso |
| —OC$_4$H$_9$—sec. | —OC$_4$H$_9$—sec. |
| —OC$_4$H$_9$—tert. | —OC$_4$H$_9$—tert. |
| —OCH$_3$ | —OC$_3$H$_7$—n |
| —OCH$_3$ | —OC$_3$H$_7$—iso |
| —OCH$_3$ | —OC$_4$H$_9$—n |
| —OCH$_3$ | —OC$_4$H$_9$—iso |
| —OCH$_3$ | —OC$_4$H$_9$—sec. |
| —OCH$_3$ | —OC$_4$H$_9$—tert. |
| —OC$_2$H$_5$ | —OC$_3$H$_7$—n |
| —OC$_2$H$_5$ | —OC$_3$H$_7$—iso |
| —OC$_2$H$_5$ | —OC$_4$H$_9$—n |
| —OC$_2$H$_5$ | —OC$_4$H$_9$—iso |
| —OC$_2$H$_5$ | —OC$_4$H$_9$—sec. |
| —OC$_2$H$_5$ | —OC$_4$H$_9$—tert. |
| —OC$_3$H$_7$—n | —OC$_3$H$_7$—iso |
| —OC$_3$H$_7$—n | —OC$_4$H$_9$—n |
| —OC$_3$H$_7$—n | —OC$_4$H$_9$—iso |
| —OC$_3$H$_7$—n | —OC$_4$H$_9$—sec. |
| —OC$_3$H$_7$—n | —OC$_4$H$_9$—tert. |
| —OC$_3$H$_7$—i | —OC$_4$H$_9$—n |
| —OC$_3$H$_7$—i | —OC$_4$H$_9$—iso |
| —OC$_3$H$_7$—i | —OC$_4$H$_9$—sec. |
| —OC$_3$H$_7$—i | —OC$_4$H$_9$—tert. |
| —OC$_4$H$_9$—n | —OC$_4$H$_9$—sec. |
| —OC$_4$H$_9$—n | —OC$_4$H$_9$—tert. |
| —OC$_4$H$_9$—iso | —C$_4$H$_9$—sec. |
| —OC$_4$H$_9$—iso | —OC$_4$H$_9$—tert. |
| —O—CH$_2$CH$_2$—O— | |
| —O—CH$_2$CH$_2$CH$_2$—O— | |
| —O—CH$_2$—C(CH$_3$)$_2$—CH$_2$—O | |

TABLE 1-continued $$\begin{array}{c} R^1 \\ \phantom{R^1}\diagdown\!\!\!\!\parallel\!\!O \\ \phantom{R^1}\phantom{\diagdown}P\!\!-\!\!CHCl_2 \\ \phantom{R^1}\diagup \\ R^2 \end{array} \qquad (II)$$

| $R^1$ | $R^2$ |
|---|---|
| —O—CH(CH$_3$)—CH$_2$—O— | |
| —O—CH(CH$_3$)—CH(CH$_3$)—O— | |

Starting substances of the formula (II) are known and can be prepared by processes which are known per se (Tetrahedron Letters 1975, 609–610).

Formula (III) provides a definition of the acid halides also to be used as starting substances for process variant (a). In this formula, $R^3$ preferably or particularly preferably represents those radicals which have already been mentioned as preferred or as particularly preferred in the context of the definitions of the substituents for formula (I); Hal represents chlorine or bromine.

Examples which may be mentioned of starting substances of the formula (III) are: the chlorides and bromides of butyric acid, isobutyric acid, valeric acid, isovaleric acid, caproic acid and cyclopropanecarboxylic acid.

Acid halides of the formula (III) are known and can be prepared by customary methods.

The isocyanates of the formula (IV) can also be used as starting substances for process variant (a). In this formula, $R^6$ preferably represents alkyl with 3 to 6 carbon atoms or cycloalkyl with 3 to 6 carbon atoms. $R^6$ particularly preferably represents alkyl with 3 to 6 carbon atoms.

Examples which may be mentioned of starting substances of the formula (IV) are: n-propyl, i-propyl, n-butyl, i-butyl, sec.-butyl and tert.-butyl isocyanates.

The isocyanates of the formula (IV) are generally known compounds of organic chemistry.

Formula (V) provides a definition of the phosphorylmethylcarbonyl compounds to be used as starting substances for process variant (b). In this formula, $R^1$, $R^2$, $R^3$ and X preferably or particularly preferably represent those radicals which have already been mentioned as preferred or as particularly preferred in the context of the definition of the substituents for formula (I).

Examples which may be mentioned of the starting substances of the formula (V) are:

TABLE 2

$$\begin{array}{c} R^1\phantom{aa} O \phantom{aaa} O \\ \phantom{R^1}\diagdown\!\!\!\!\parallel \phantom{aaa} \parallel \\ \phantom{R^1}\phantom{\diagdown}P\!\!-\!\!CH\!\!-\!\!C\!\!-\!\!R^3 \\ \phantom{R^1}\diagup \phantom{aa} | \\ R^2 \phantom{aaa} X \end{array} \qquad (V)$$

| $R^1$ | $R^2$ | X | $R^3$ |
|---|---|---|---|
| —OC$_3$H$_7$—i | —OC$_3$H$_7$—i | H | —OCH$_2$—N⟨pyrrole⟩ |
| —OC$_3$H$_7$—i | —OC$_3$H$_7$—i | H | —O—CH(CH$_3$)—COOC$_4$H$_9$—n |

TABLE 2-continued $$\begin{array}{c}R^1\phantom{xx}O\phantom{xxxx}O\\\diagdown\phantom{x}\|\phantom{xxx}\|\\P-CH-C-R^3\\\diagup\phantom{x}|\\R^2\phantom{xx}X\end{array}\quad(V)$$

| R¹ | R² | X | R³ |
|---|---|---|---|
| —OC₃H₇—i | —OC₃H₇—i | H | —O—C(CH₃)H—COOC₂H₅ |
| —OC₃H₇—i | —OC₃H₇—i | H | —OCH(CH₃)-pyrazolyl |
| —C₆H₅ | —OC₃H₇—i | H | —OCH(CH₃)-pyrazolyl |
| —C₆H₅ | —OC₃H₇—i | H | —OCH(C₂H₅)-pyrazolyl |
| —OC₃H₇—i | —OC₃H₇—i | H | —OCH(C₃H₇-n)-pyrazolyl |
| —OC₃H₇—i | —OC₃H₇—i | H | —OCH₂-(3-CH₃-pyrazolyl) (also 5-CH₃) |
| —OC₃H₇—i | —OC₃H₇—i | H | —CH₂CH(CH₃)₂ |
| —OC₃H₇—i | —OC₃H₇—i | H | cyclopropyl |
| —OC₃H₇—i | —OC₃H₇—i | H | —OCH₂—COOC₂H₅ |
| —OC₃H₇—i | —OC₃H₇—i | H | —OCH₂—COOC₄H₉—n |
| —OC₃H₇—n | —OC₃H₇—n | Cl | —CH₂CH(CH₃)₂ |
| —OC₃H₇—i | —OC₃H₇—i | Cl | —CH(CH₃)₂ |
| —OC₄H₉—i | —OC₄H₉—i | Cl | —CH₂CH(CH₃)₂ |
| —OC₃H₇—i | —OC₃H₇—i | H | —CH(CH₃)₂ |
| —OC₄H₉—sec. | —OC₄H₉—sec. | Cl | —CH₂CH(CH₃)₂ |
| —OC₃H₇—i | —OC₃H₇—i | Cl | —C₃H₇—n |
| —OC₃H₇—n | —OC₃H₇—n | Cl | —CH₂CH(CH₃)₂ |
| —OC₃H₇—i | —OC₃H₇—i | H | —C₃H₇—n |
| —OC₄H₉—i | —OC₄H₉—i | H | —CH₂CH(CH₃)₂ |
| —OC₃H₇—i | —OC₃H₇—i | H | —OCH(C₃H₇-i)-pyrazolyl |
| —OC₃H₇—i | —OC₃H₇—i | H | —OCH(C₂H₅)-pyrazolyl |
| —C₆H₅ | —OC₃H₇—i | H | —OCH₂COOC₂H₅ |
| —C₆H₅ | —OC₃H₇—i | H | —OCH₂COOC₄H₉—n |
| —C₆H₅ | —OC₃H₇—i | H | —OCH(CH₃)COOC₂H₅ |
| —C₆H₅ | —OC₃H₇—i | H | —OCH(CH₃)COOC₄H₉—n |
| —C₆H₅ | —OC₃H₇—i | H | —OCH₂-(3,5-diCH₃-pyrazolyl) |
| —OC₄H₉—n | —OC₄H₉—n | H | —OCH₂-(3,5-diCH₃-pyrazolyl) |
| —OC₄H₉—n | —OC₄H₉—n | H | —OCH(CH₃)-pyrazolyl |
| —OC₄H₉—n | —OC₄H₉—n | H | —OCH₂-pyrazolyl |
| —OC₄H₉—n | —OC₄H₉—n | H | —OCH(C₂H₅)-pyrazolyl |
| —OC₄H₉—n | —OC₄H₉—n | H | —OCH(C₃H₇-i)-pyrazolyl |

TABLE 2-continued

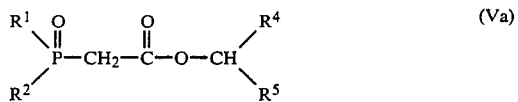

| R¹ | R² | X | R³ |
|---|---|---|---|
| —OC$_3$H$_7$—n | —OC$_3$H$_7$—n | H | —OCH—N(N=)C$_3$H$_7$—i |
| —OC$_4$H$_9$—n | —OC$_4$H$_9$—n | H | —OCH$_2$COOC$_2$H$_5$ |
| —OC$_3$H$_7$—n | —OC$_3$H$_7$—n | H | —OCH$_2$COOC$_2$H$_5$ |
| —OC$_4$H$_9$—n | —OC$_4$H$_9$—n | H | —OCH$_2$COOC$_4$H$_9$—n |
| —OC$_3$H$_7$—n | —OC$_3$H$_7$—n | H | —OCH$_2$COOC$_4$H$_9$—n |
| —OC$_3$H$_7$—n | —OC$_3$H$_7$—n | Cl | —CH(CH$_3$)$_2$ |
| —OC$_3$H$_7$—n | —OC$_3$H$_7$—n | H | —CH(CH$_3$)$_2$ |
| —OC$_3$H$_7$—n | —OC$_3$H$_7$—n | Cl | —C$_3$H$_7$—n |
| —OC$_3$H$_7$—n | —OC$_3$H$_7$—n | H | —C$_3$H$_7$—n |

Some of the starting compounds of the formula (V) have not yet been described in the literature. For example, the compounds of the formula (Va)

in which
R¹, R², R⁴ and R⁵ have the abovementioned meanings,
are new.

The new compounds of the formula (Va) are obtained by a process in which compounds of the formula (VI)

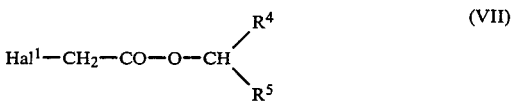

in which
R¹ and R² have the abovementioned meanings and
R¹⁰ represents optionally substituted C$_1$–C$_4$-alkyl or benzyl,
are heated with halogenoacetic acid esters of the formula (VII)

$$\text{Hal}^1\text{—CH}_2\text{—CO—O—CH}\begin{matrix}R^4\\R^5\end{matrix} \quad \text{(VII)}$$

in which
R⁴ and R⁵ have the abovementioned meanings and
Hal¹ represents halogen, in particular chlorine or bromine,
to temperatures between 50° C. and 200° C., preferably between 100° C. and 150° C., and the reaction products of the formula Hal¹-R¹⁰ are removed, if appropriate under reduced pressure.

The compounds of the formula (VI) are generally known compounds of organic chemistry.

Examples which may be mentioned are: the tri-n-propyl ester, tri-i-propyl ester, tri-n-butyl ester, tri-i-butyl ester and tri-sec.-butyl ester of phosphorous acid, and the di-n-propyl ester, di-i-propyl ester, di-n-butyl ester, di-i-butyl ester and di-sec.-butyl ester of phenyl-phosphonous acid.

The halogenoacetic acid esters of the formula (VII) are new. The compounds of the formula (VII) are obtained by reacting halogenoacetic acid halides of the formula (VIII)

in which
Hal¹ and Hal² represent halogen, in particular chlorine or bromine,
with hydroxy derivatives of the formula (IX)

in which
R⁴ and R⁵ have the abovementioned meanings, in the presence of acid acceptors, such as, for example, triethylamine, and in the presence of diluents, such as, for example, methylene chloride, at temperatures between −50° C. and +100° C., preferably between −20° C. and +50° C.

Working up can be carried out by customary methods, for example by washing the organic solution with aqueous sodium bicarbonate solution, drying and filtering the organic phase and distilling off the solvent under reduced pressure.

The starting compounds of the formula (VIII) are generally known compounds of organic chemistry.

The hydroxy derivatives of the formula (IX) are already known (compare, for example, German No. 2,835,158).

Process variant (a) is preferably carried out using diluents.

Suitable diluents are virtually all the inert organic solvents. These include, in particular, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and dimethylsulphoxide, tetramethylenesulphone, hexamethylphosphoric acid triamide and pyridine.

Process variant (a) is preferably carried out in the presence of acid acceptors. These preferably include alkali metal and alkaline earth metal hydrides, such as, for example, sodium hydride and calcium hydride, organometallic compounds, such as, for example, butyllithium or isopropylmagnesium chloride, alcoholates, such as, for example, potassium tert.-butanolate and aluminum isopropylate, and specific amines, such as, for example, diazabicyclooctane, diazabicycloundecene and pyridine.

The reaction temperature can be varied within a substantial range in process (a) for the preparation of the compounds of the formula (I). In general, the reaction is carried out between −120° C. and +100° C., preferably at −70° C. to +50° C. Process (a) is in general carried out under normal pressure.

Equimolar amounts of the starting substances of the formulae (II) and (III) or (II) and (IV) and, in addition, 1 to 2, preferably 1.0 to 1.4, molar equivalents of a suitable base are in general employed for carrying out process (a).

In general, the dichloromethanephosphonic acid derivative of the formula (II) and the base are brought together in a suitable solvent, if appropriate with cooling, and the acid halide of the formula (III) or the isocyanate of the formula (IV) is slowly added, if appropriate in solution. The reaction mixture is stirred until the reaction has ended. Working up can be carried out by customary methods, for example by acidification, for example with sulphuric acid, extraction with methylene chloride, drying and filtration of the organic constituents under reduced pressure and moderately elevated temperature. The residues of low volatility essentially contain compounds of the formula (I), which are characterized by their physico-chemical properties.

Process (b) is carried out using chlorinating agents. Chlorinating agents which may be mentioned are chlorine, sulphuryl chloride and alkali metal or alkaline earth metal hypochlorites, such as, for example, sodium hypochlorite (if appropriate in the form of so-called hypochlorite solution) or calcium hypochlorite. Hypochlorite solution is preferably used.

Process (b) is preferably carried out in the presence of diluents. Possible diluents are, in particular, halogenated hydrocarbons, such as, for example, methylene chloride, ethylene chloride, chloroform and carbon tetrachloride. If hypochlorite solution is employed, water is used as the diluent, and is supplemented, if necessary, by an inert organic solvent.

If appropriate, acid acceptors are used in process (b). If aqueous hypochlorite solutions are employed, the corresponding alkali metal hydroxides or alkaline earth metal hydroxides, such as, for example, sodium hydroxide, potassium hydroxide or calcium hydroxide or calcium hydroxide, are preferably used as the acid-binding agents.

The reaction temperatures can be varied within a substantial range in process (b). In general, the reaction is carried out between −20° C. and +50° C., preferably at 0° C. to 30° C. The process is in general carried out under normal pressure.

For carrying out process (b), between 0.5 and 5, preferably between 0.9 and 3.5, molar equivalents of chlorinating agent are in general employed per mole of phosphorylmethylcarbonyl compound of the formula (V), and the pH value is in general kept between 7 and 14, preferably between 9 and 14.

In general, the chlorinating agent and the diluent are initially introduced into the reaction vessel and the compound of the formula (V) is added, with vigorous stirring. When the reaction has ended, the mixture can be worked up by customary methods, for example by washing the organic solution with aqueous sodium bicarbonate solution, drying and filtering the organic phase and distilling off the solvent under reduced pressure at moderately elevated temperature. The residues of low volatility essentially contain the compounds of the formula (I), which are characterized by their physico-chemical properties.

The active compounds of the formula (I) according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention also exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating rice diseases such as Pyricularia oryzae.

The active compounds can be converted to the customary formulations, such as solutions, emulsions, suspensions, powders, foams, pastes, granules, aerosols, very fine capsules in polymeric substances and in coating compositions for seed, and ULV formulations.

These formulations are produced in known manner, for example by mixing the active compounds with extenders, that is, liquid solvents and/or solid carriers, optionally with the use of surface-active agents, that is, emulsifying agents and/or dispersing agents, and/or foam-forming agents.

In the case of the use of water as an extender, organic solvnts can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example petroleum fractions and mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly-dispersed silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

The known herbicides which are suitable for the mixtures are, for example, 1-amino-6-ethylthio-3-(2,2-dimethylpropyl)-1,3,5-triazine-2,4(1H,3H)-dione or N-(2-benzothiazolyl)-N,N'-dimethyl-urea, for combating weeds in cereals; 4-amino-3-methyl-6-phenyl-1,2,4-triazin-5(4H)-one, for combating weeds in sugarbeet and 4-amino-6-(1,1-dimethylethyl)-3-methylthio-1,2,4-triazin-5(4H)-one for combating weeds in soy beans.

Mixing with other known active compounds, such as fungicides, insecticides, acaricides, nematicides, bird repellants, plant nutrients and agents which improve soil structure, is also possible.

The active compounds can be used as such or in the form of their formulations or the use forms prepared therefrom by further dilution, such as ready-to-use solutions, emulsions, suspensions, powders, pastes and granules. They are used in the customary manner, for example by watering, spraying, atomizing, scattering, immersion, misting, vaporizing, injecting, forming a slurry, brushing on, dusting, dry dressing, moist dressing, wet dressing, slurry dressing or encrusting.

The active compounds according to the invention can be applied either before or after emergence of the plants. They are preferably applied before emergence of the plants, that is to say by the pre-emergence method. They can also be incorporated into the soil before sowing.

The amount of active compound used can vary within a substantial range. It depends essentially on the nature of the desired effect. In general, the amounts used are between 0.05 and 10 kg of active compound per ha, preferably between 0.1 and 5 kg/ha.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The examples which follow serve to illustrate the invention further.

PREPARATION EXAMPLES

EXAMPLE 1

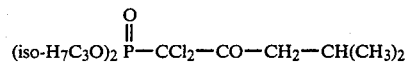

(Process variant a)

37.4 g (0.15 mole) of diisopropyl dichloromethanephosphonate are initially introduced into 100 ml of tetrahydrofuran, the mixture is cooled to −70° C. and 100 ml of a 15% strength solution of butyl-lithium in n-hexane are added. The mixture is stirred at −70° C. for one hour, 18.1 g (0.15 mole) of isovaleryl chloride are added and the mixture is stirred at −70° C. for a further hour. 50 ml of 1N sulphuric acid are slowly added dropwise at a temperature of 0° C.; the mixture is then extracted three times with methylene chloride, the organic phase is dried and filtered and the solvent is distilled off under reduced pressure.

34.8 g (69% of theory) of 1,1-dichloro-1-(O,O-di-i-propyl-phosphoryl)-4-methyl-pentan-2-one of refractive index $n_D^{20}$ 1.4455 are obtained.

EXAMPLE 2

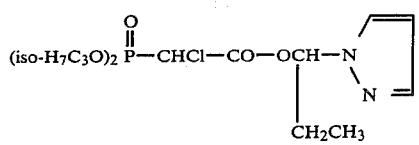

(Process variant b)

28 g of hypochlorite solution (containing 11.9% of "active chlorine") are initially introduced into 100 ml of carbon tetrachloride and the mixture is cooled to 0° C. to 5° C. 13.3 g (0.04 mole) of 1-(pyrazol-1-yl)-n-propyl 1-(O,O-di-i-propyl-phosphoryl)-acetate in 50 ml of carbon tetrachloride are added dropwise, with vigorous stirring. The mixture is subsequently stirred at 0° C. for 5° C. for 2 hours and washed with sodium bicarbonate solution, the organic phase is dried over sodium sulphate, filtered and concentrated and the residue is subjected to incipient distillation under a vapour pump at 70° C. for 10 minutes.

6.7 g (46% of theory) of 1-(pyrazol-1-yl)-n-propyl 1-chloro-1-(O,O-di-i-propyl-phosphoryl)-acetate are obtained in the form of an oil of refractive index $n_D^{20}$ 1.4557.

The compounds of the formula (I) listed in Table 3 which follows were prepared analogously to Example 1 and 2, or analogously to process variant (a) or (b):

TABLE 3

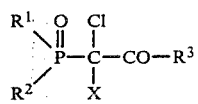

(I)

| Example No. | $R^1$ | $R^2$ | X | $R^3$ | Refractive index $n_D^{20}$ |
|---|---|---|---|---|---|
| 3 | —OC$_3$H$_7$—iso | —OC$_3$H$_7$—iso | Cl | —CH(CH$_3$)$_2$ | 1.4367 |
| 4 | —OC$_3$H$_7$—iso | —OC$_3$H$_7$—iso | Cl | —NH—CH(CH$_3$)$_2$ | 1.4550 |
| 5 | —OC$_3$H$_7$—iso | —OC$_3$H$_7$—iso | Cl | —NH—CH(C$_2$H$_5$)(CH$_3$) | 1.4546 |
| 6 | —OC$_3$H$_7$—iso | —OC$_3$H$_7$—iso | Cl | —OCH(CH$_3$)—COOC$_4$H$_9$—n | 1.4385 |
| 7 | —OC$_3$H$_7$—iso | —OC$_3$H$_7$—iso | Cl | —OCH(CH$_3$)—COOC$_2$H$_5$ | 1.4432 |
| 8 | —OC$_3$H$_7$—iso | —OC$_3$H$_7$—iso | Cl | cyclopropyl | 1.4611 |
| 9 | —OC$_3$H$_7$—iso | —OC$_3$H$_7$—iso | Cl | —OCH$_2$—N(3,5-dimethylpyrazolyl) | 1.4681 |
| 10 | —OC$_3$H$_7$—iso | —OC$_3$H$_7$—iso | H | —OCH(C$_3$H$_7$-n)—N-pyrazolyl | 1.4658 |
| 11 | phenyl | —OC$_3$H$_7$—iso | Cl | —OCH(CH$_3$)—N-pyrazolyl | 1.5265 |
| 12 | —OC$_3$H$_7$—iso | —OC$_3$H$_7$—iso | H | —OCH(C$_2$H$_5$)—N-(4-chloropyrazolyl) | 1.4711 |

TABLE 3-continued $$\begin{matrix} R^1 & O & Cl \\ & \backslash \| & | \\ & P-C-CO-R^3 \\ & / & | \\ R^2 & & X \end{matrix} \qquad (I)$$

| Example No. | R¹ | R² | X | R³ | Refractive index $n_D^{20}$ |
|---|---|---|---|---|---|
| 13 | —OC₃H₇—iso | —OC₃H₇—iso | H | —OCH₂—N(pyrazole with CH₃, Cl, CH₃ substituents) | 1.4795 |
| 14 | —OC₃H₇—iso | —OC₃H₇—iso | Cl | —OCH(C₂H₅)—N(pyrazole) | 1.4585 |
| 15 | —OC₄H₉—n | —OC₄H₉—n | H | —OCH(C₂H₅)—N(pyrazole) | 1.4618 |
| 16 | —OC₄H₉—n | —OC₄H₉—n | Cl | —OCH(C₂H₅)—N(pyrazole) | 1.4648 |
| 17 | —OC₄H₉—iso | —OC₄H₉—iso | Cl | —CH₂CH(CH₃)₂ | |
| 18 | —OC₄H₉—sec. | —OC₄H₉—sec. | Cl | —CH₂CH(CH₃)₂ | |
| 19 | —C₆H₅ | —OC₃H₇—iso | H | —O—CH(CH₃)—N(pyrazole) | 1.5295 |
| 20 | —OC₃H₇—iso | —OC₃H₇—iso | H | —OCH₂—N(pyrazole with CH₃, CH₃) | 1.4689 |
| 21 | —OC₄H₉—n | —OC₄H₉—n | H | —OCH₂—N(pyrazole with CH₃, CH₃) | 1.4694 |
| 22 | —C₆H₅ | —OC₃H₇—iso | Cl | —O—CH(C₂H₅)—N(pyrazole) | 1.5183 |
| 23 | —OCH₂CH₂Cl | —OCH₂CH₂Cl | Cl | —O—CH(C₂H₅)—N(pyrazole) | 1.5009 |

PREPARATION OF THE STARTING SUBSTANCES OF THE FORMULA (Va)

EXAMPLE (Va-1)

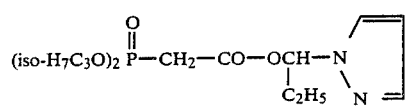

A mixture of 16.2 g (0.08 mole) of 1-(pyrazol-1-yl)-1-n-propyl 1-chloro-acetate and 18.4 g (0.088 mole) of tri-isopropyl phosphite is stirred at 140° C. for 4 hours and is then subjected to incipient distillation under a vapor pump at 70° C. for 10 minutes.

22.7 g (85% of theory) of 1-(pyrazol-1-yl)-n-propyl 1-(O,O-di-isopropyl-phosphoryl)-acetate of refractive index $n_D^{20}$ 1.4567 are obtained.

The remaining compounds of the formula (Va) listed in Table 4 were prepared analogously to Example (Va-1):

TABLE 4

$$\underset{R^2}{\overset{R^1}{\diagdown}}\underset{}{\overset{O}{\underset{\|}{P}}}-CH_2-CO-O-CH\underset{R^5}{\overset{R^4}{\diagup}} \quad (Va)$$

| Example No. | R¹ | R² | R⁴ | R⁵ | Refractive index $n_D^{20}$ |
|---|---|---|---|---|---|
| Va-2 | —OC₃H₇—iso | —OC₃H₇—iso | CH₃ | —COOC₄H₉—n | |
| Va-3 | —OC₃H₇—iso | —OC₃H₇—iso | CH₃ | —COOC₂H₅ | |
| Va-4 | —OC₃H₇—iso | —OC₃H₇—iso | —C₃H₇—iso | pyrazolyl | 1.4538 |
| Va-5 | —OC₃H₇—iso | —OC₃H₇—iso | H | 3,5-dimethylpyrazolyl | 1.4635 |
| Va-6 | —OC₃H₇—iso | —OC₃H₇—iso | —C₃H₇—n | pyrazolyl | 1.4595 |
| Va-7 | —OC₃H₇—iso | —OC₃H₇—iso | CH₃ | pyrazolyl | 1.4539 |
| Va-8 | phenyl | —OC₃H₇—iso | CH₃ | —COOC₂H₅ | 1.4818 |
| Va-9 | phenyl | —OC₃H₇—iso | CH₃ | pyrazolyl | 1.4293 |
| Va-10 | phenyl | —OC₃H₇—iso | CH₃ | —COOC₄H₉—n | 1.4765 |
| Va-11 | —OC₃H₇—iso | —OC₃H₇—iso | H | pyrazolyl | 1.4579 |

TABLE 4-continued $$\underset{R^2}{\overset{R^1}{\phantom{|}}}\overset{O}{\underset{\|}{P}}-CH_2-CO-O-CH\underset{R^5}{\overset{R^4}{\phantom{|}}} \quad (Va)$$

| Example No. | R¹ | R² | R⁴ | R⁵ | Refractive index $n_D^{20}$ |
|---|---|---|---|---|---|
| Va-12 | –C₆H₅ (phenyl) | —OC₃H₇—iso | H | CH₃ group with pyrazole (–N–N=C(CH₃)–, with CH₃) | 1.5229 |
| Va-13 | —OC₄H₉—n | —OC₄H₉—n | H | CH₃ group with pyrazole (–N–N=C(CH₃)–, with CH₃) | 1.4673 |
| Va-14 | —OC₄H₉—n | —OC₄H₉—n | —C₂H₅ | pyrazol-1-yl | 1.4618 |
| Va-15 | –C₆H₅ (phenyl) | —OC₃H₇—iso | —C₂H₅ | pyrazol-1-yl |  |

PREPARATION OF THE STARTING SUBSTANCES OF THE FORMULA (VII)

EXAMPLE (VII-1)

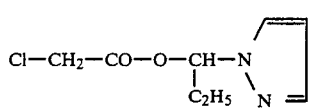

12.6 g (0.1 mole) of 1-hydroxy-1-(pyrazol-1-yl)-propane are initially introduced into 100 ml of methylene chloride, the mixture is cooled to 0° C. to 10° C. with ice, 13.3 g (0.13 mole) of triethylamine are added, and 11.3 g (0.10 mole) of chloroacetyl chloride are then slowly added dropwise at 0° C. to 10° C., with vigorous stirring. The mixture is subsequently stirred for 15 to 20 minutes, washed three times with sodium bicarbonate solution, dried and evaporated and the residue is subjected to incipient distillation under a vapor pump at 20° C.

11.3 g (56% of theory) of 1-(pyrazol-1-yl)-n-propyl 1-chloro-acetate of refractive index $n_D^{20}$ 1.4875 are obtained.

The remaining compounds of the formula (VII) listed in Table 5 were obtained analogously to Example (VII-1):

TABLE 5

$$Hal^1-CH_2-CO-O-CH\underset{R^5}{\overset{R^4}{\phantom{|}}} \quad (VII)$$

| Example No. | Hal¹ | R⁴ | R⁵ | Physical constant |
|---|---|---|---|---|
| VII-2 | Cl | CH₃ | pyrazol-1-yl | $n_D^{20}$: 1.4962 |
| VII-3 | Cl | H | 3-methylpyrazol-1-yl | melting point: 58° C. |
| VII-4 | Cl | CH₃ | —COOC₂H₅ |  |
| VII-5 | Cl | CH₃ | —COOC₄H₉ |  |
| VII-6 | Cl | n-C₃H₇ | pyrazol-1-yl | $n_D^{20}$: 1.4920 |
| VII-7 | Cl | iso-C₃H₇ | pyrazol-1-yl | $n_D^{20}$: 1.4869 |

TABLE 5-continued $$Hal^1-CH_2-CO-O-CH\underset{R^5}{\overset{R^4}{\diagup}}\quad (VII)$$

| Example No. | Hal$^1$ | R$^4$ | R$^5$ | Physical constant |
|---|---|---|---|---|
| VII-8 | Cl | H | -N(pyrazolyl) | |
| VII-9 | Br | CH$_3$ | -N(pyrazolyl) | |
| VII-10 | Br | H | -N(4-methylpyrazolyl) | |
| VII-11 | Br | C$_2$H$_5$ | -N(pyrazolyl) | |

PREPARATION OF THE STARTING SUBSTANCES OF THE FORMULA (IX)

EXAMPLE (IX-1)

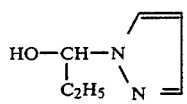

34 g (0.5 mole) of pyrazole are initially introduced into 250 ml of methylene chloride, and 47 g (0.65 mole) of propionaldehyde are added dropwise at 0° C. to 5° C. The mixture is stirred for about 72 hours and subjected to incipient distillation at 20° C. under a waterpump vacuum.

42 g (67% of theory) of 1-hydroxy-1-(pyrazol-1-yl)-n-propane are obtained as a colorless oil.

The following compounds of the formula (IX) listed in Table 6 were obtained analogously to Example (IX-1):

TABLE 6

$$HO-CH\underset{R^5}{\overset{R^4}{\diagup}}\quad (IX)$$

| Example No. | R$^4$ | R$^5$ | Physical constant |
|---|---|---|---|
| IX-2 | CH$_3$ | -N(pyrazolyl) | |
| IX-3 | H | -N(3-methylpyrazolyl) | 88° C. |
| IX-4 | n-C$_3$H$_7$ | -N(pyrazolyl) | |
| IX-5 | iso-C$_3$H$_7$ | -N(pyrazolyl) | |

EXAMPLE A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, for example, the following compound according to the preparation examples exhibits an excellent activity: (1).

EXAMPLE B

Pre-emergence test—greenhouse
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, for example, the following compound according to the preparation examples exhibits an excellent activity: (9).

EXAMPLE C

Pyricularia test (rice)/systemic
Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of Pyricularia oryzae. Thereafter, the plants remain in a greehouse at a temperature of 25° C. and a relative atmospheric humidity of 100% until they are evaluated.

Evaluation of the disease infestation is carried out 4 days after the inoculation.

In this test, a clearly superior fungicidal activity compared with the prior art is shown, for example, by the compounds according to the following preparation examples: (6), (7) and (8), and the rice plants are not injured.

It is understood that the specification and examples are illustrative but not limitative of the present invention and that other embodiments within the spirit and scope of the invention will suggest themselves to those skilled in the art.

We claim:

1. A chlorinated phosphorylmethylcarbonyl derivative of the formula $$\begin{array}{c} R^1 \quad O \quad Cl \\ \diagdown \parallel \quad | \\ P-C-CO-R^3 \\ \diagup \quad | \\ R^2 \quad X \end{array}$$

in which
R$^1$ represents radicals from the series comprising alkyl with up to 6 carbon atoms, alkoxy with up to 6 carbon atoms and aralkyl and aralkoxy with 6 to 10 carbon atoms in the aryl part and up to 2 carbon atoms in the alkyl part, in each case optionally monosubsituted or polysubsttuted by halogen or C$_1$-C$_4$-alkoxy, or represents phenyl which is optionally monosubstituted or polysubstituted by halogen, nitro, C$_1$-C$_4$-alkyl, C$_1$-C$_4$-alkoxy and/or C$_1$-C$_4$-alkoxycarbonyl, and
R$^2$ represents alkoxy with up to 6 carbon atoms or aralkoxy with 6 to 10 carbon atoms in the alkyl part and up to 2 carbon atoms in the alkyl part, in each case optionally monosubstituted or polysubstituted by halogen or C$_1$-C$_4$-alkoxy, or R$^1$ and R$^2$ together represent a branched or straight-chain alkanedioxy radical with 2 to 5 carbon atoms in the alkyl part,
X represents hydrogen or chlorine and
R$^3$ represents the grouping $$-\underset{\underset{R^5}{|}}{O}CH-R^4$$

in which
R$^4$ represents hydrogen or alkyl with up to 4 carbon atoms and
R$^5$ represents an alkoxycarbonyl radical with up to 4 carbon atoms in the alkyl part or represents an optionally substituted pyrazolyl radical $$-N\underset{\diagdown}{\overset{R^7 \quad R^8}{\diagup}}_{\underset{R^9}{N=}}$$

wherein
R$^7$ and R$^9$ are identical or different and represent hydrogen or C$_1$-C$_4$ alkyl and
R$^8$ represents hydrogen, halogen or C$_1$-C$_4$-alkyl; or
if X represents chlorine, R$^3$ also may represent cycloalkyl with 3 to 6 carbon atoms, which is optionally monosubstituted or polysubstituted by C$_1$-C$_3$-alkyl.

2. A chlorinated phosphorylmethylcarbonyl derivative according to claim 1,
in which
R$^1$ represents n-propoxy, i-propoxy, n-butoxy, i-butoxy, sec.-butoxy or tert.-butoxy,
R$^2$ represents n-propoxy, i-propoxy, n-butoxy, i-butoxy, sec.-butoxy or tert.-butoxy,
X represents chlorine and
R$^3$ represents cyclopropyl.

3. A chlorinated phosphorylmethylcarbonyl derivative according to claim 1,
in which
R$^1$ represents n-propoxy, i-propoxy, n-butoxy, i-butoxy, sec.-butoxy, tert.-butoxy or phenyl,
R$^2$ represents n-propoxy, i-propoxy, n-butoxy, i-butoxy, sec.-butoxy or tert.-butoxy,
X represents chlorine and
R$^3$ represents the grouping $$-OCH\underset{\diagdown}{\overset{\diagup R^4}{\phantom{X}}}_{R^5}$$

in which
R$^4$ represents methyl or ethyl and
R$^5$ represents methoxycarbonyl, ethoxycarbonyl, n-propoxycarbonyl, i-propoxycarbonyl, n-butoxycarbonyl, i-butoxycarbonyl, sec.-butoxycarbonyl or tert.-butoxycarbonyl.

4. A chlorinated phosphorylmethylcarbonyl derivative according to claim 1,
in which
R$^1$ represents n-propoxy, i-propoxy, n-butoxy, i-butoxy, sec.-butoxy, tert.-butoxy or phenyl, $R^2$ represents n-propoxy, i-propoxy, n-butoxy, i-butoxy, sec.-butoxy or tert.-butoxy, X represents hydrogen or chlorine and $R^3$ represents the grouping

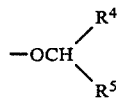

in which $R^4$ represents hydrogen, methyl, ethyl, n-propyl or i-propyl and $R^5$ represents an optionally substituted pyrazolyl radical

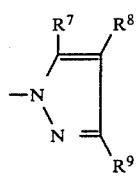

wherein $R^7$ and $R^9$ are identical or different and represent hydrogen or methyl and $R^8$ represents hydrogen or chlorine.

5. A compound according to claim 1, wherein such compound is 1-butoxycarbonyl-ethyl 1,1-dichloro-1-(O,O-di-i-propyl-phosphoryl)-acetate of the formula

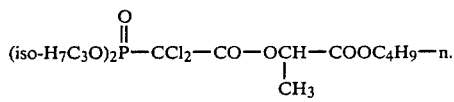

6. A compound according to claim 1, wherein such compound is 1-ethoxycarbonyl-ethyl 1,1-dichloro-1-(O,O-di-i-propyl-phosphoryl)-acetate of the formula

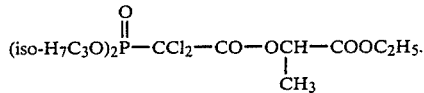

7. A compound according to claim 1, wherein such compound is 1,1-dichloro-1-(O,O-di-i-propyl-phosphoryl)-2-cyclopropyl-ethan-2-one of the formula

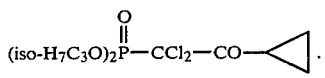

8. A compound according to claim 1, wherein such compound is (3,5-dimethyl-pyrazol-1yl)-methyl 1,1-dichloro-1-(O,O-di-i-propyl-phosphoryl)-acetate of the formula

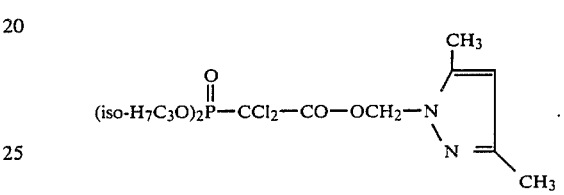

9. A fungicidal and selectively herbicidal composition comprising a fungicidally and selectively herbicidally effective amount of a compound according to claim 1 in admixture with a diluent.

10. A method of combating fungi and undesired plants which comprises administering to such fungi or plants or to a habitat thereof a fungicidally or selectively herbicidally effective amount of a compound according to claim 1.

11. The method according to claim 10, wherein the compound is applied to rice or to an area in which rice is to be grown and is 1-butoxycarbonyl-ethyl 1,1-dichloro-1-(O,O-di-i-propyl-phosphoryl)-acetate, 1-ethoxycarbonyl-ethyl 1,1-dichloro-1-(O,O-di-i-propyl-phosphoryl)-acetate, 1,1-dichloro-1-(O,O-di-i-propyl-phosphoryl)-2-cyclopropyl-ethan-2-one or (3,5-dimethyl-pyrazol-1-yl)-methyl 1,1-dichloro-1-(O,O-di-i-propyl-phosphoryl)-acetate.

* * * * *

UNITED STATES PATENT AND TRADEMARK OFFICE
CERTIFICATE OF CORRECTION

PATENT NO. : 4,541,858
DATED : September 17, 1985
INVENTOR(S) : Theodor Pfister, et al.

It is certified that error appears in the above-identified patent and that said Letters Patent is hereby corrected as shown below:

| | |
|---|---|
| Col. 5, line 61 | Delete "-$C_4H_9$-sec." and substitute -- -$OC_4H_9$-sec. -- |
| Col. 7, line 55, under "R'" | Delete "-$OC_3H_7$-n" and substitute -- -$OC_3H_7$-i -- |
| Col. 11, lines 45,46 | Delete "or calcium hydroxide" second instance |
| Col. 13, line 15 | Correct spelling of "solvents" |
| Col. 25, line 59 | Correct spelling of "polysubstituted" |
| Col. 26, line 28 | Delete "c4" and substitute --$C_4$-- |
| Col. 28, line 16 | After "pyrazol-1" insert -- - $\frac{4}{-}$ -- |

Signed and Sealed this

Fourth Day of February 1986

[SEAL]

Attest:

DONALD J. QUIGG

Attesting Officer

Commissioner of Patents and Trademarks